United States Patent
Abrams et al.

(10) Patent No.: US 10,772,857 B2
(45) Date of Patent: Sep. 15, 2020

(54) HIGH CONCENTRATION MEDICANT SOLUTIONS FOR TREATING NEUROLOGICAL DISORDERS

(71) Applicant: Cerebral Therapeutics, Inc., Aurora, CO (US)

(72) Inventors: Daniel J. Abrams, Aurora, CO (US); Thomas Joseph Anchordoguy, Lakewood, CO (US)

(73) Assignee: Cerebral Therapeutics, Inc., Aurora, CO (US)

( * ) Notice: Subject to any disclaimer, the term of this patent is extended or adjusted under 35 U.S.C. 154(b) by 0 days.

(21) Appl. No.: 16/168,614

(22) Filed: Oct. 23, 2018

(65) Prior Publication Data

US 2019/0117600 A1   Apr. 25, 2019

Related U.S. Application Data

(60) Provisional application No. 62/575,770, filed on Oct. 23, 2017.

(51) Int. Cl.
| | | |
|---|---|---|
| *A61K 31/19* | (2006.01) | |
| *A61K 9/00* | (2006.01) | |
| *A61P 25/18* | (2006.01) | |
| *A61P 25/24* | (2006.01) | |
| *A61P 25/08* | (2006.01) | |
| *A61K 47/12* | (2006.01) | |
| *A61K 45/06* | (2006.01) | |

(52) U.S. Cl.
CPC ............ *A61K 31/19* (2013.01); *A61K 9/0019* (2013.01); *A61K 9/0085* (2013.01); *A61K 45/06* (2013.01); *A61K 47/12* (2013.01); *A61P 25/08* (2018.01); *A61P 25/18* (2018.01); *A61P 25/24* (2018.01)

(58) Field of Classification Search
CPC ........ A61K 31/19; A61K 45/06; A61K 47/12; A61K 9/0019; A61K 9/0085; A61P 25/08; A61P 25/18; A61P 25/24
See application file for complete search history.

(56) References Cited

U.S. PATENT DOCUMENTS

| | | | | |
|---|---|---|---|---|
| 5,095,033 A | * | 3/1992 | Levy | A61K 31/36 514/464 |
| 5,707,663 A | * | 1/1998 | Ayer | A61K 9/0004 424/473 |
| 8,447,407 B2 | * | 5/2013 | Talathi | A61B 5/0476 607/45 |
| 2005/0037992 A1 | * | 2/2005 | Lyons | A61K 31/165 514/49 |
| 2005/0090548 A1 | * | 4/2005 | Hildebrand | A61K 31/195 514/561 |
| 2007/0083063 A1 | | 4/2007 | Nelson et al. | |
| 2016/0122282 A1 | | 5/2016 | Kandula | |

FOREIGN PATENT DOCUMENTS

| | | |
|---|---|---|
| WO | WO 1994/027587 | 12/1994 |
| WO | WO 2008/115919 | 9/2008 |
| WO | WO 2009/014762 | 1/2009 |
| WO | WO 2009/151741 | 12/2009 |

OTHER PUBLICATIONS

Rogawski, (Neurotherapeutics: The J of Am Soc for Exp. NeuroTherapeutics, 6, 344-351, Apr. 2009). (Year: 2009).*
Serralta et al. (Epilepsy Research, 20, 2006, p. 15-26) (Year: 2006).*
Barcia et al. (Neurotherapeutics: The J of Am Soc for Experimental NeuroTherapeutics, 6, 337-343, Apr. 2009) (Year: 2009).*
Abrams, Daniel J. "Feasibility of Delivery of Anti-Epilepsy Medications into the Cerebrospinal Fluid (10802)", Neuromodulation, vol. 19, No. 3, Dec. 10, 2015, p. e107.

* cited by examiner

*Primary Examiner* — Umamaheswari Ramachandran
(74) *Attorney, Agent, or Firm* — Bozicevic, Field & Francis LLP; Karl Bozicevic

(57) ABSTRACT

Highly concentrated solutions are disclosed along with methods of inhibiting and/or ameliorating functional neurological disorders of the brain. The method may include administering directly to a brain of a subject a medicament multiple times over a time period of at least two days. The medicament may include a half-life of less than 2 hour in the cerebrospinal fluid. The method may include inhibiting and/or ameliorating a functional neurological disorder of the brain using the medicant.

14 Claims, 6 Drawing Sheets

HIGH CONCENTRATION MEDICANT SOLUTIONS FOR TREATING NEUROLOGICAL DISORDERS

CROSS-REFERENCE

This application claims the benefit of U.S. Provisional Application No. 62/575,770, filed Oct. 23, 2017, which application is incorporated herein by reference.

FIELD OF THE INVENTION

The present disclosure generally relates to direct brain administration of a medicant and includes solutions of a highly concentrated drug/medicant as well as methods of administering medicants to subjects to treat functional neurological disorders.

BACKGROUND OF THE INVENTION

The delivery of medications directly to specific parts of the body has several advantages over systemic administration. Lower doses of medication can be used with site specific administration and systemic toxicities of drug therapies can be mitigated. Furthermore, delivery port implantable devices are used regularly in the delivery of chemotherapy and medications to allow direct administration of certain medications best administered through direct access to the venous system, central nervous system and peritoneal cavity.

In some organs of the body, direct administration of certain drugs may be required to achieve therapeutic doses of medication without inducing serious toxicity. For example, the blood-brain barrier (BBB) protects the brain from potentially toxic substances, but also restricts the passage of most drug molecules. Because of the BBB, direct administration of drugs may be required to achieve therapeutic concentrations for the treatment of cancer, neurodegenerative diseases such as Alzheimer's (AD) and Parkinson's Disease (PD), and other conditions.

Alternatively, devices for local, repeatable, and chronic drug delivery can be used. These devices contain catheters that distribute drug to specific tissues and may or may not contain a reservoir for storing drug. These devices include implantable drug pump systems, for example, Ommaya Rickham reservoirs and Port-A-Cath® devices. These devices deliver either a bolus or slow infusion of drugs to specific regions of the body. The types of drugs that can be used range from pain medications (e.g., morphine) to chemotherapeutics (e.g., methotrexate, cytarabine).

Cerebrospinal fluid (CSF) is a clear, colorless, body fluid found in the brain and spinal cord. CSF is produced in the choroid plexuses of the ventricles of the brain and absorbed in the arachnoid granulations. There is about 125 mL of CSF at any one time, and about 500 mL is generated every day. CSF acts, in part, as a cushion for the brain, providing basic mechanical and immunological protection to the brain inside the skull. The CSF also serves a vital function in cerebral autoregulation of cerebral blood flow. Chronic administration of small molecule medications to the brain CSF is unexplored especially medications with short half-lives. The only two molecules that have ever been looked at chronically are morphine and baclofen which have barely been explored but have been used because they already have been used in CSF administration in the spine. Baclofen's half-life is on the order of five hours and morphine's half-life is on the order of two hours.

Acute administration has been looked at primarily in the form of short term boluses and primarily for treatment of leptomeningeal disease. In fact, it has been decided that chronic administration of drugs into the CSF will not work for brain disease other than for leptomeningeal disease which is not within the brain itself CSF flow is typically thought to go from the brain to one lateral ventricle, to the third ventricle and fourth and out over and under the brain convexities before being reabsorbed. In addition, animals have vastly different size and scale to their brains and they unexplored relative to other bodily organs and systems. The animals used in most testing of CSF flow is rats who have a 111000 the size of the human brain and even primates have a brain which is at best ⅒th the size of the human brain for large experimental primates. Furthermore, clinical results are expected to be different in human subjects than in animals. As a result of these and other factors allometric scaling is expected to be vastly off Allometric equations take the general form Y=aM h, where Y is some biological variable, M is a measure of body size, and b is some scaling exponent. In allometry, equations are often presented in logarithmic form so that a diverse range of body sizes can be plotted on a single graph.

It would be desirable, therefore, to determine a method, system, composition, and/or protocol resulting in the successful chronic administration of medications with short half-lives directly to the brain.

SUMMARY OF THE INVENTION

Highly concentrated solutions are disclosed along with methods of inhibiting and/or ameliorating functional neurological disorders of the brain. The method may include administering directly to a brain of a subject a medicament multiple times over a time period of 2, 3, 4, 6, 6, 7 days or more. The medicament may include a half-life of less than one day, 16 hours, 8 hours, 4 hours or 2 hours in the cerebrospinal fluid. The method may include inhibiting and/or ameliorating a functional neurological disorder of the brain using the medicament.

In some embodiments, the medicament may include valproic acid or pharmaceutically active derivatives thereof. In some embodiments, the medicament comprises a half-life of less than about 30 minutes in the cerebrospinal fluid. In some embodiments, during treatment the medicament is continuously delivered in an amount so as to maintain a concentration in the cerebrospinal fluid of between 1 to 500 micrograms/ml, or 5 to 200 micrograms/ml or 50 micrograms/ml ±20%, ±10%, ±5% over a period of 1, 2, 3, 4, 5, 6, 7 or more days. In some embodiments, there is a substantially linear relationship between a concentration of the medicament in the cerebrospinal fluid and a daily dosage of the medicament.

The functional neurological disorder may include, Epilepsy, Status Epilepticus, Bipolar, Bipolar Spectrum Disorder, Post Traumatic Stress Disorder or Other Epilepsy, Bipolar Spectrum and Anxiety Related Disorder.

In some embodiments, administering directly via a catheter to the cerebrospinal fluid of a subject's brain may include substantially continuous administration of the medicament during treatment via a catheter to the cerebrospinal fluid. In some embodiments, dosage is based upon a desired daily dosage of the medicament and the medicament's half-life in the cerebrospinal fluid. Administering directly to a subject's brain may include continuously administering a dosage of the medicament such that a concentration of about 50 micrograms/ml ±20%, ±10%, ±5% over a period of 1, 2, 3, 4, 5, 6, 7 or more days is maintained in the cerebrospinal fluid during a treatment period effective to provide a meaningful therapeutic benefit to the patient.

In some embodiments, administering directly via a catheter to the cerebrospinal fluid to a subject's brain may include administering multiple bolus pulses of the medicament during treatment. A dosage may be based upon a target treatment dosage of the medicament and the medicament's half-life in the cerebrospinal fluid such that the target treatment dosage during a treatment period is multiplied by a number of half-lives lost occurring during the gaps in the treatment period to achieve a meaningful target therapeutic levels. Administering directly to a subject's brain comprises administering multiple bolus pulses a dosage of the medicament such that an average concentration of 1 to 500 micrograms/ml, or 5 to 200 micrograms/ml or 50 micrograms/ml ±20%, ±10%, ±5%, is maintained in the cerebrospinal fluid during a treatment period of time sufficient to provide a meaningful benefit to the patient.

In some embodiments, the medicament may include valproic acid or pharmaceutically active derivatives thereof. The dosage may be determined using a relationship defined by valproic acid concentration in micrograms per milliliter is approximately equivalent to dose in valproic acid dose mg/day. So for example a concentration of 50 milligrams per day is equal to approximately 50 micrograms per ml.

In some embodiments, the method may include monitoring administration of the medicament by monitoring a subject's perception of the subject's body temperature.

In some embodiments, the medication may be only administered to one lateral brain ventricle on one side of the brain and not bilaterally administered to both ventricles.

In some embodiments the medication maybe administered to the third ventricle, cisterna magna, or basilar cisterns.

In some embodiments, the concentration may be determined by sampling cerebrospinal fluid from the lateral ventricle or third ventricle or cisterna *Magna* or basilar cisterns and determining a concentration of the medicament and/or a derivative thereof to adjust up or down the infusion amount (by changing the daily flow rate and/or the concentration of the infused medication) to achieve an improvement in the clinical symptoms.

In some embodiments, a chemical compound may function to inhibit and/or ameliorate functional neurological disorders of the brain. The chemical compound may include a medicament administering directly to a brain of a subject. The medicament may be administered as part of a pharmaceutical composition. The medicament may include a half-life of less than 0.5, 1, 2, 4, 8 or 16 hours in the cerebrospinal fluid. The medicament may inhibit and/or ameliorate and/or modify a functional neurological disorder of the brain. The medicament may include a solubility of 10, 25, 50, 100 or 200 mg/ml.

In some embodiments, the medicament comprises valproic acid or pharmaceutically active derivatives thereof. The dosage may be determined using a relationship defined by log (valproic acid concentration) is approximately equivalent to log (valproic acid dose mg/day) minus a fixed number between about 3 to about 30.

In some embodiments of the invention, additional excipient materials are included within the formulation with the drug which may be valproic acid. The excipients can be citric acid which can be a form of a citrate and be present in an amount in a range of 0.1 to 4% by weight or 0.2 to 2% by weight or 0.4%±10%. The formulation may also include an acetate buffer in a concentration of one to 25 millimolar or 10 millimolar, a sodium phosphate buffer in an amount of 10 to 50 millimolar or about 20 millimolar, and saline in an amount of 10 to 50 millimolar or about to 20 millimolar.

These and other objects, advantages, and features of the invention will become apparent to those persons skilled in the art upon reading the details of the formulations, uses thereof and methods of treatment as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

Figure 1:
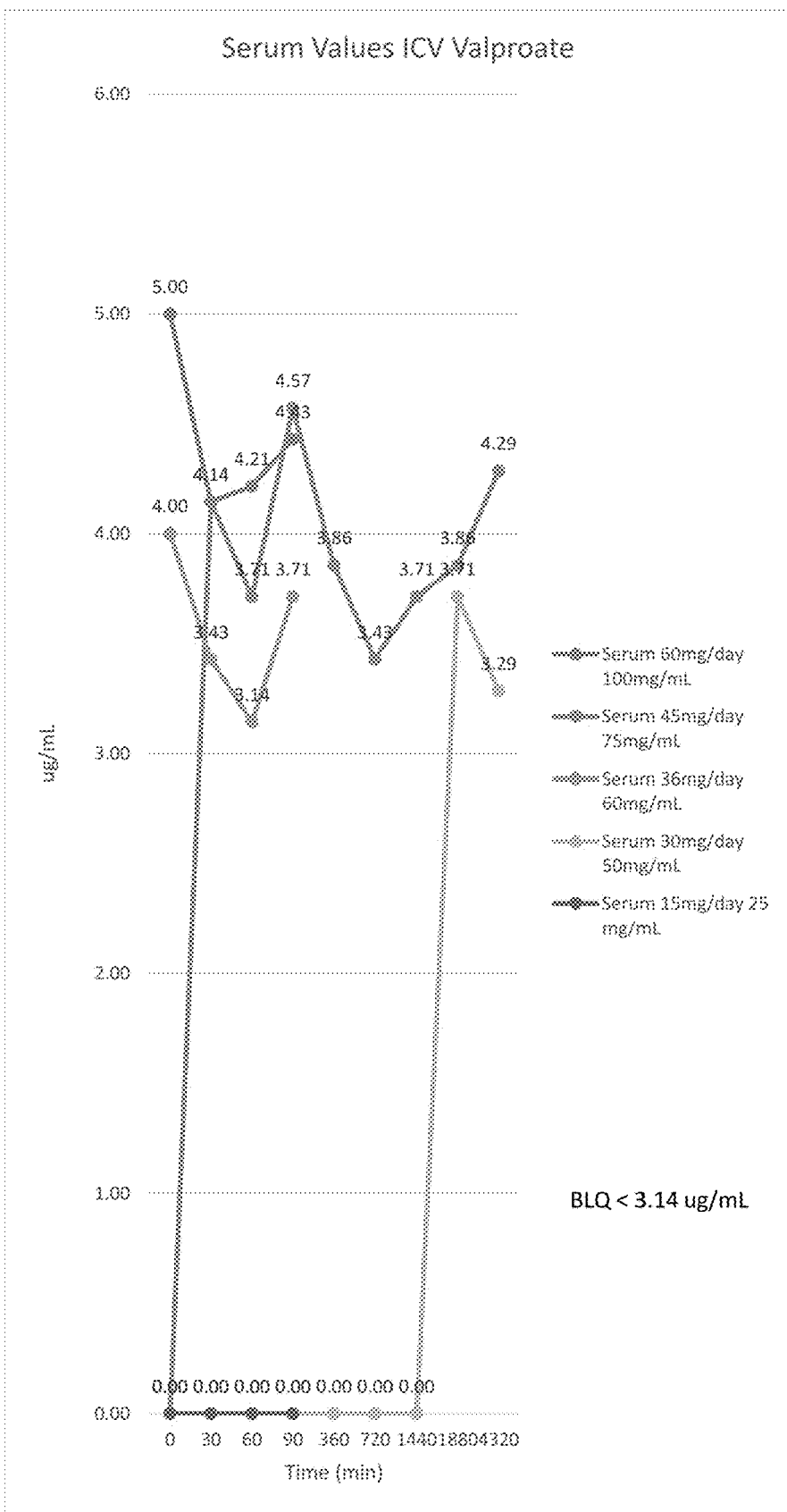
FIG. 1 depicts a graph of a concentration of valproate in blood serum of human subjects over time after the valproate has stop being administered for a week.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die" electrically connected to the module substrate" does not preclude scenarios in which a "fourth die electrically connected to the module substrate"

is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only and is not intended to limiting. As used in this specification and the appended claims, the singular forms "a", "an", and "the" include singular and plural referents unless the content clearly dictates otherwise. Thus, for example, reference to "a linker" includes one or more linkers.

It is to be understood that terms such as "about" or "substantially" or other similar terms when used in combination with numerical descriptors are interpreted as meaning +/−10% unless defined alternatively herein and/or as defined by the state of the art.

DETAILED DESCRIPTION OF THE INVENTION

Before the present formulations, uses thereof and methods of treatment are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an administration" includes a plurality of such administrations or doses and reference to "the bolus" includes reference to one or more bolus doses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Unless defined otherwise, all technical and scientific terms used herein have the same meaning as commonly understood by one of ordinary skill in the art.

The terms "administration," "administering," or the like, as used herein when used in the context of providing a pharmaceutical, cosmeceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "bolus" as used herein generally refers to a single dose of a drug or other medicinal preparation given all at once.

The term "catheter" as used herein generally refers to medical devices that can be inserted in the body to treat diseases or perform a surgical procedure.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The terms "effective concentration" or "effective amount" as used herein generally refers to a sufficient amount of the pharmaceutically active agent that is added to decrease, prevent or inhibit the growth of a virus and/or cancerous growth. The amount will vary for each compound and upon known factors related to the item or use to which the pharmaceutically active agent is applied.

The term "functional neurological disorder" as used herein generally refers to a condition in which a brain of a subject is structurally normal (or at least has no significant structural abnormalities), but functions incorrectly. The disorder may lead to the subject experiencing neurological symptoms such as weakness, movement disorders, sensory symptoms, seizures, and blackouts.

The terms "in need of treatment" or "in need thereof" when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers but include knowledge that the individual or animal is ill, will be ill, or is at risk of becoming ill, as the result of a condition that may be ameliorated or treated with the specified medical intervention.

The term "malady" as used herein generally refers to any disorder or disease of the body or any undesirable or disordered condition including, but not limited to, illness, sickness, affliction, complaint, ailment, indisposition, virus, disease, fungus, infection, disease, etc.

The term "medicant" as used herein generally refers a medicinal substance used or to prevent, cure, or relieve disease.

Terms such as "pharmaceutical composition," "pharmaceutical formulation," "pharmaceutical preparation," or the like, are used herein to generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

The term "pharmacologically inert," as used herein, generally refers to a compound, additive, binder, vehicle, and the like, that is substantially free of any pharmacologic or "drug-like" activity.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects. The term "subject" as used herein generally refers to a mammal, and in particular to a human.

The phrase "therapeutically effective amount" generally refers to an amount of a drug or pharmaceutical composition that will elicit at least one desired biological or physiological response of a cell, a tissue, a system, animal or human that is being sought by a researcher, veterinarian, physician or other caregiver.

ADMINISTRATION EMBODIMENTS

Herein described is a very short half-life medicant useful for treating a disease of the brain. Typically, medicants used for treating diseases of the rain, especially functional neurological disorder, have relatively long half-lives on the order of two hours or longer, and except for morphine, typically much longer than two hours. The reasons medicants with long half-lives are used is obvious and due at least in part to the fact that it is difficult to achieve therapeutic levels of a medicant in a subject if the medicant is decomposing too quickly. This can be especially problematic due to the manner in which medicants are typically administered in a general matter (e.g., orally, intravenously, etc.) to a subject as opposed to a specific regional administration (e.g., topically to a regional skin condition. When medicants are administered generally (e.g., orally in order to treat a specific region of the body not orally associated) they can take time to diffuse through the subject's body and accumulate in appreciable levels in the specific region requiring medicants with a substantial half-life.

In some embodiments, a chemical composition and/or method may include inhibiting and/or ameliorating functional neurological disorders of the brain. In some embodiments, functional neurological disorders of the brain may include epilepsy. In other embodiments, functional neurological disorders of the brain may include Bipolar and Bipolar Spectrum Disorder. In some embodiments, the functional neurological disorder may include Post Traumatic Stress Disorder or Other Anxiety Related Disorder.

The term "functional neurological disorder" as used herein generally refers to a condition in which a brain of a subject is structurally normal (or at least has no significant structural abnormalities), but functions incorrectly. The disorder may lead to the subject experiencing neurological symptoms such as weakness, movement disorders, sensory symptoms, seizures, and blackouts.

The method may include administering one or more medicants directly to a brain of a subject. A medicant may be administered chronically. Generally chronic administration may include any medicant paradigm where the medicant is given during more than one experimental session. However, it should be noted that each experimental session may involve multiple doses or drug doses and behavioral paradigms. Typically, a paradigm may be considered chronic if it was repeated over many days for a subject Chronic administration may include multiple times over a time period of at least two days. In contrast acute administration of a medicant may be generally defined as a drug administration paradigm where a drug is given during one experimental session (once during the experiment, or multiple times) within a 24-hour period.

Chronic administration may include continuous administration of a medicant during a treatment period. In some embodiments, administering directly to a subject's brain may include substantially continuous administration of the medicant during treatment.

In some embodiments, administering directly to a subject's brain may include administering multiple bolus pulses of the medicant during treatment. Bolus pulses in general may be described as the administration of a medicant in a single, large dose which might be repeated after an interval of days. Thought to have the advantage of high tissue levels and fewer of the undesirableside-effects associated with more frequent dosing. In some embodiments, herein bolus pulses may be considered as the administration of a medicant multiple times wherein the time between administration is greater than a half-life of the medicant. A dosage may be based upon a target treatment dosage of the medicant and the medicant's half-life in the cerebrospinal fluid such that the target treatment dosage during a treatment period is multiplied by a number of half-lives lost occurring during the gaps in the treatment period to achieve a meaningful target therapeutic levels.

Figure 2:
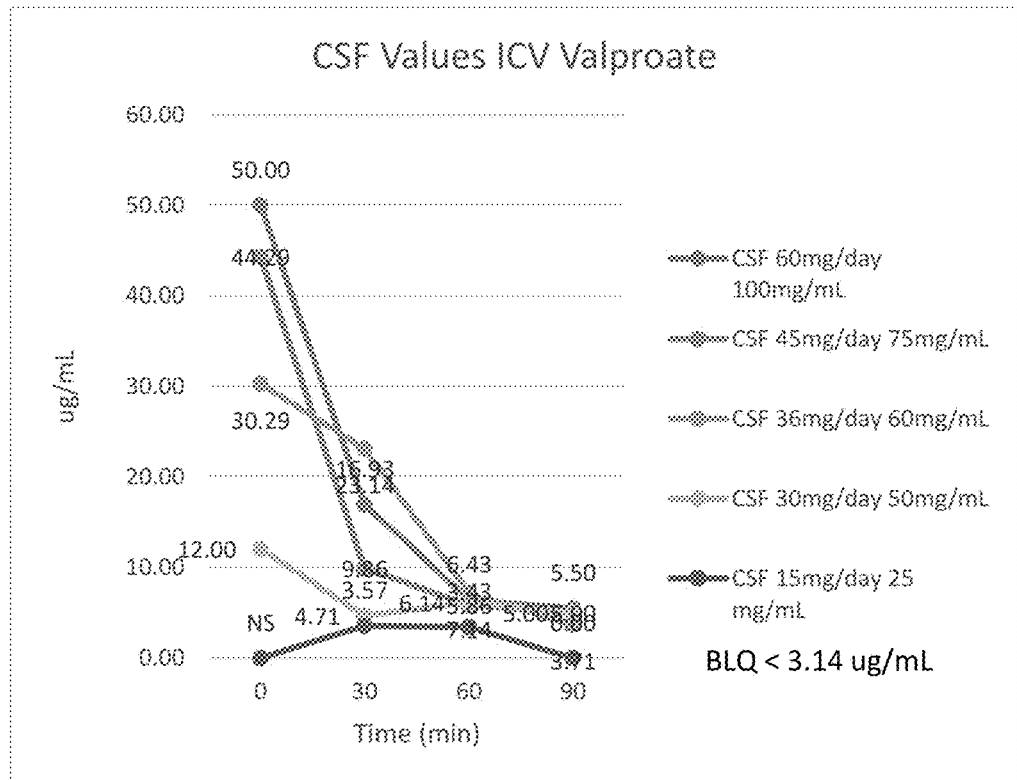
FIG. 2 depicts a graph of a concentration of valproate in cerebrospinal fluid of human subjects over time after the valproate has stop being administered for a week.
Figure 3:
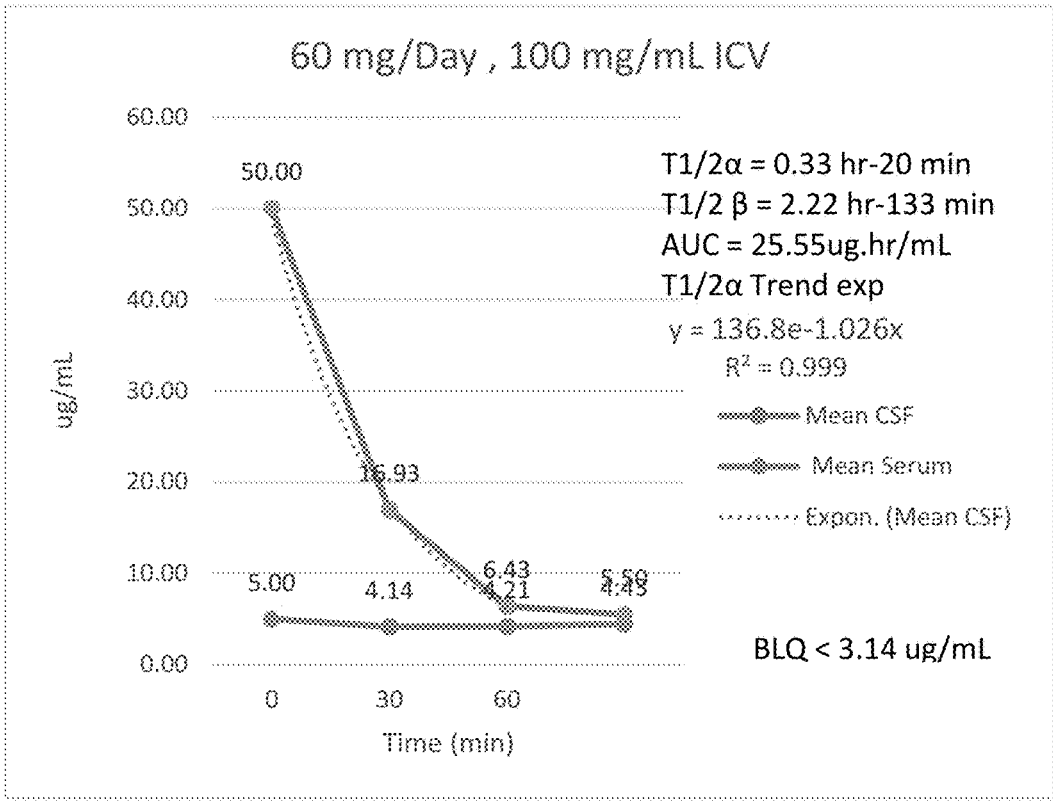
FIG. 3 depicts a graph of a concentration of valproate in cerebrospinal fluid and blood serum of a human subject over time after the valproate has stop being administered for a week.

In some embodiments, a dosage is based upon a desired daily dosage of the medicant and the medicant's half-life in the cerebrospinal fluid. Cerebrospinal fluid medicant concentration levels are a better predictor of concentration levels of the medicant in the brain relative to, for example, blood serum levels which are not a good predictor and unreliable. FIG. 1 depicts a graph of a concentration of valproate in blood serum of human subjects over time after the valproate has stop being administered for a week. The subjects have been administered different dosage levels of valproate using different concentrations of valproate in solution. As can be seen in FIG. 1 valproate concentrations were quite erratic and unpredictable relative to the valproate dosage. FIG. 2 depicts a graph of a concentration of valproate in cerebrospinal fluid of human subject over time after the valproate has stop being administered for a week. The subjects have been administered different dosage levels of valproate using different concentrations of valproate in solution. As can be seen the concentration of valproate drops quickly as would be expected due to the short half-life of valproate. FIG. 3 depicts a graph of a concentration of valproate in cerebrospinal fluid and blood serum of a human subject over time after the valproate has stop being administered for a week. The subject has been administered 60 mg/day total of valproate using a pump which provides direct regional administration of valproate to the subject's brain using a 100 mg/mL solution. FIG. 3 further demonstrates that testing cerebrospinal fluid is a far better predictor of medicant concentrations than is serum.

Figure 4:
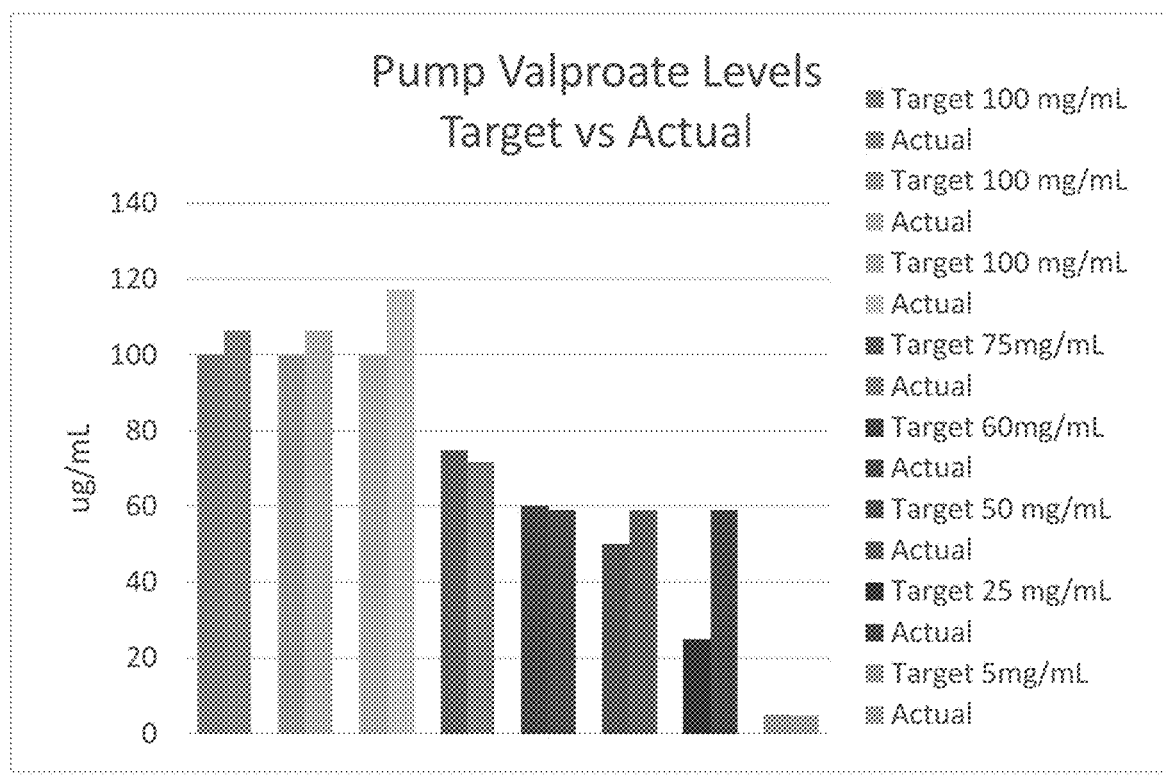
FIG. 4 depicts a graph of targeted concentration of valproate in cerebrospinal fluid verses an actual concentration of valproate in cerebrospinal fluid.

In some embodiments, a substantially linear relationship between a concentration of the medicant in the cerebrospinal fluid and a daily dosage of the medicant. In some embodiments, the concentration of the medicant and/or a derivative thereof may be determined by sampling cerebrospinal fluid from the lateral ventricle to adjust up or down the infusion amount (by changing the daily flow rate and/or the concentration of the infused medication) to achieve an improvement in the clinical symptoms. This linear relationship allows for a greatly increased chance of a caregiver accurately hitting a desired valproate dosage target FIG. 4 depicts a graph of targeted concentration of valproate in cerebrospinal fluid verses an actual concentration of valproate in cerebrospinal fluid.

In some embodiments, the dosage may be determined using a relationship defined by log (valproic acid concentration) is approximately equivalent to log (valproic acid dose mg/day).

The dosage may be determined using a relationship defined by log (valproic acid concentration) is equivalent to log (valproic acid dose mg/day) minus a fixed number between about 0 to about. In some embodiments, the dosage may be determined using a relationship defined by log (valproic acid concentration) is equivalent to log (valproic acid dose mg/day) minus a fixed number between about 3 to about 30.

In some embodiments, the medicant may include valproic acid or pharmaceutically active derivatives thereof. The dosage may be determined using a relationship defined by log (valproic acid concentration) is approximately equivalent to log (valproic acid dose mg/day). The dosage may be determined using a relationship defined by log (valproic acid concentration) 10 is equivalent to log (valproic acid dose mg/day) minus 3.

Figure 5:
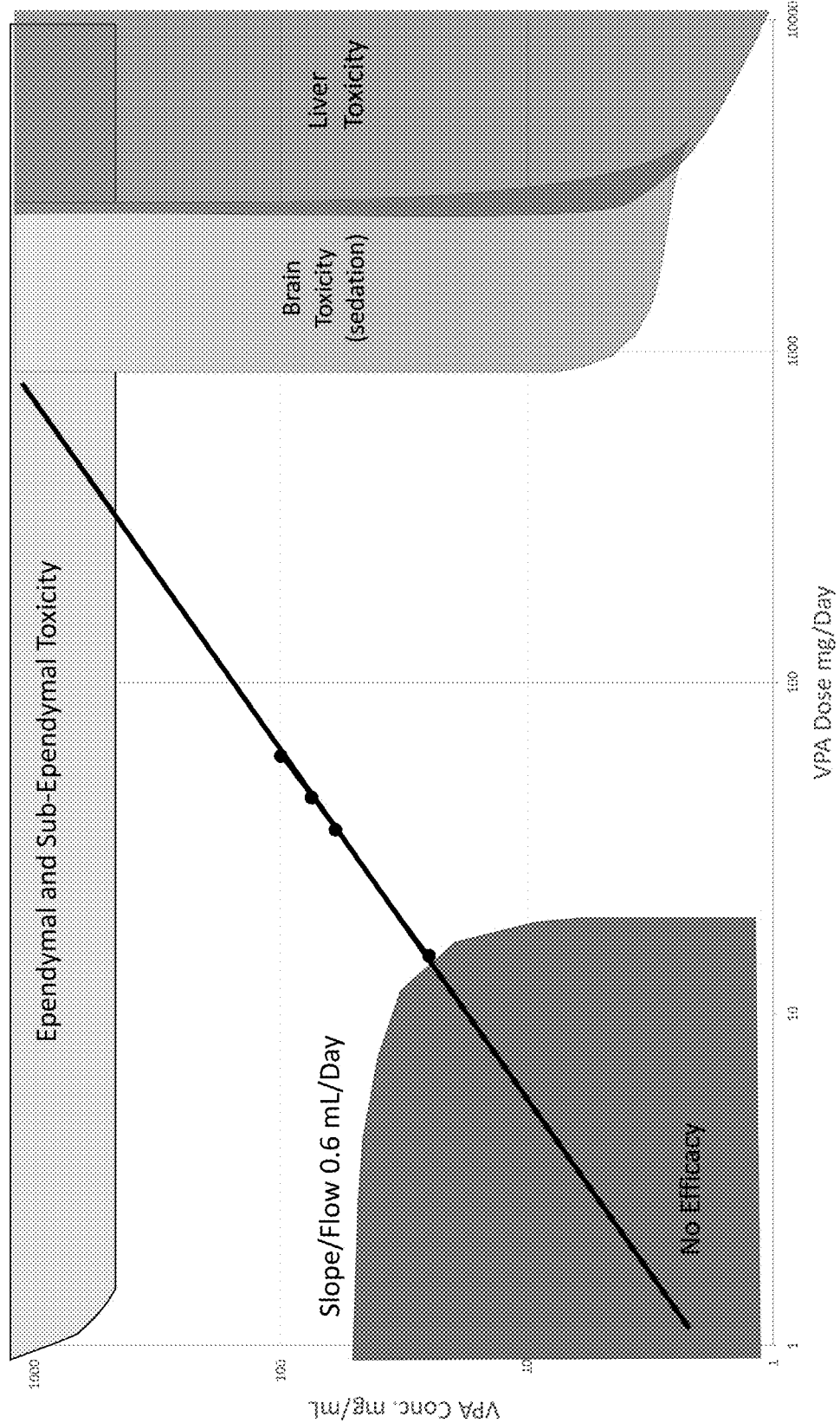
FIG. 5 depicts a graph of a relationship between valproic acid concentration cerebrospinal fluid and a dosage of valproic acid.
Figure 6:
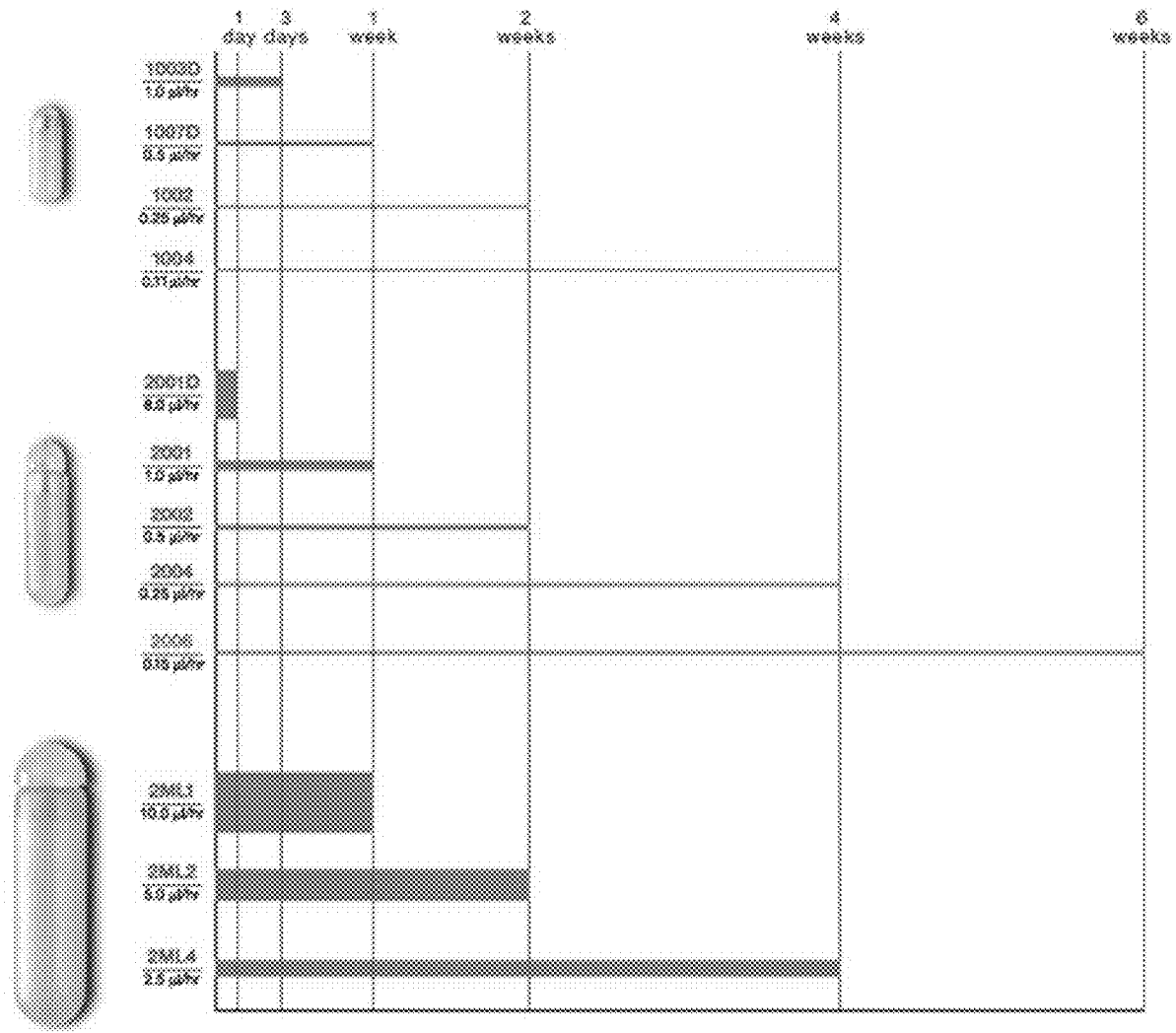
FIG. 6 depicts a graph of how long it takes to reach a targeted concentration of valproate using different dosage rates.

One must have the cerebrospinal fluid concentration levels high enough so that the cerebrospinal fluid drives the medicant into the brain during the natural flow of cerebrospinal fluid through the brain. FIG. 5 depicts a graph of a relationship between valproic acid concentration in cerebrospinal fluid and a dosage of valproic acid. The graph depicts the dosage range wherein no efficacy was observed as well as the dosage wherein different toxicities for various organs are known. Administering directly to a subject's brain may include administering a dosage of the medicant such that an average concentration of at least 10 micrograms/mL is maintained in the cerebrospinal fluid during a treatment period. An average concentration may be used when multiple bolus pulses are used to administer the medicant. If continuous or substantially continuous administration is used to deliver a medicant then a concentration of at least 10 micrograms/mL is maintained in the cerebrospinal fluid during a treatment period. In some embodiments, during treatment the medicant has a concentration in the cerebrospinal fluid of between about 10 micrograms/mL to about 150 micrograms/mL. FIG. 6 depicts a graph of how long it takes to reach a targeted concentration of valproate using different dosage rates. It is nonobvious to scale dosage from animals to humans. When results from animal trials have been used to scale human dosages the resulting dosages can be off by as much as 400%. Therefore, human data is very important.

In some embodiments, the medicant may include a half-life of less than 2 hour in the cerebrospinal fluid. In some preferred embodiments, the medicant may include a half-life of less than 1 hour in the cerebrospinal fluid. The method may include inhibiting and/or ameliorating a functional neurological disorder of the brain using the medicant. In some embodiments, the medicant may include valproic acid or pharmaceutically active derivatives thereof. In some embodiments, the medicant may include a half-life of less than about 30 minutes in the cerebrospinal fluid (e.g., valproic acid or pharmaceutically active derivatives thereof).

Cerebrospinal fluid flow is typically thought to go from the brain to one lateral ventricle, to the third ventricle and fourth and out over and under the brain convexities before being reabsorbed. It has been found, surprisingly and unexpectedly, that the ventricles appear to mix. In some embodiments, the medicant may be only administered to one lateral brain ventricle on one side of the brain while still administering medicant to both ventricles. Due to this discovery the medicant may not require administration bilaterally to both ventricles in order to provide medicant to both ventricles.

In some embodiments, the method may include monitoring administration of the medicant by monitoring a subject's perception of the subject's body temperature sensation and/or feeling of being nauseous. It has been found in all of a group of subjects as they have gotten to therapeutic levels of administered medicants that they have felt cold. This is an unexpected and unprecedented result and one assumes that higher medication doses have changed the hypothalamus. It was initially thought that there should be concern around the dosage but subjects rapidly acclimated to these symptoms and found a benefit. Interestingly, it tells the clinician that it is a sign of clinical improvements further discussed in the examples.

High Concentration Embodiments

Sodium valproate is used clinically at concentrations of 100 mg/mL or less. Like any weak acid, the valproate molecule will be charged above its pKa value (4.8), and thus more readily soluble at high pH. Despite its charged character at high pH, solubility limits in water are commonly reported as 50-100 mg/mL. Indeed, this is quite concentrated for any solute, with 100 mg/mL equivalent to a 10% solution. Given the reported solubility limit, it was unexpected when experiments demonstrated that sodium valproate fully dissolves and forms clear, homogeneous aqueous solutions up to at least 500 mg/mL. In some embodiments, sodium valproate may have a concentration of greater than 200 mg/mL, greater than 300 mg/mL, or greater than 400 mg/mL.

Given a pKa of 4.8, it would be expected based upon accepted generalizations that a concentrated solution of sodium valproate would have a pH within about 1 pH unit of the pKa. Therefore, a solution buffered by sodium valproate should resist pH changes between pH 3.8-5.8, with minimal buffering capacity ($\beta$) above pH 5.8. However, a solution of 150 mg/mL sodium valproate in water yields a pH of approximately 8.3. More concentrated solutions (>350 mg/mL) possess pH values above 9. This unexpected finding indicates that sodium valproate is much more soluble than is commonly reported.

Figure 7:
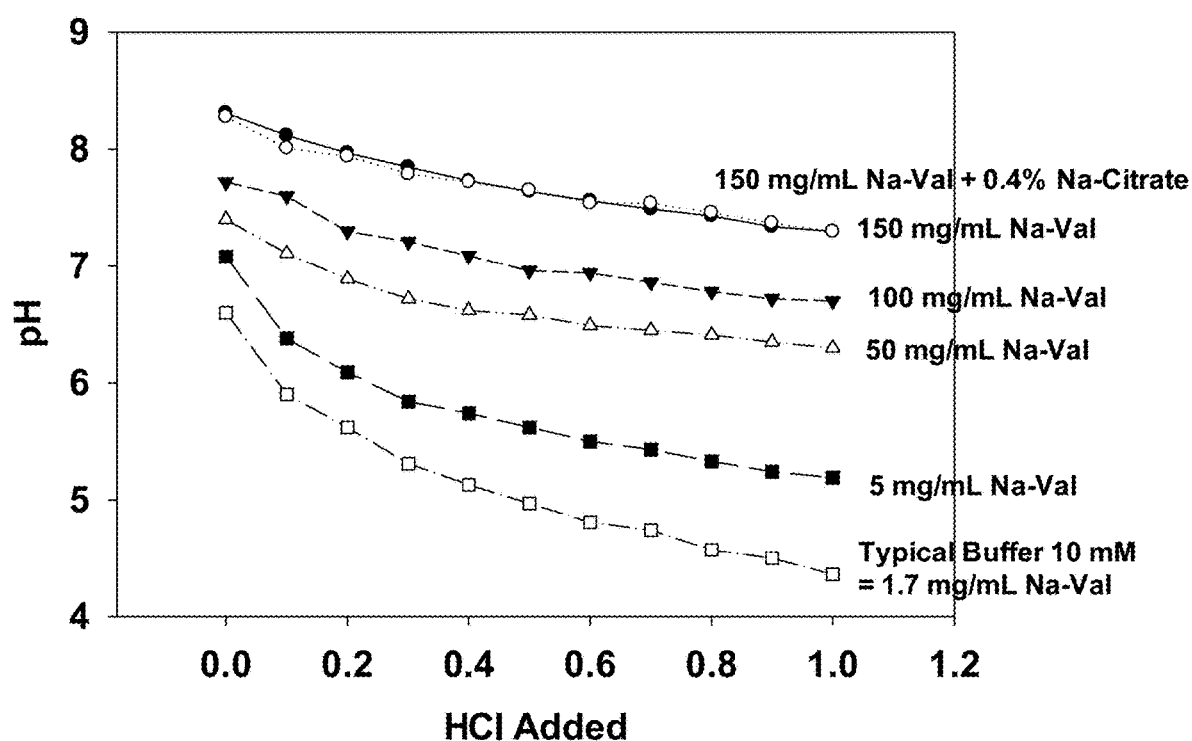
FIG. 7 depicts a graph of pH titrations of different sodium valproate solutions (5 mL) by progressively adding 0.1 mL of 25 mM HCl.

FIG. 7 depicts a graph pH titrations of different sodium valproate solutions (5 mL) by progressively adding 0.1 mL of 25 mM HCl. A typical buffer concentration is 10 mM, which is equivalent to 1.7 mg/mL sodium valproate: about 90-fold than embodiments depicted herein. If you look at the line depicting the titration of 10 mM sodium valproate (open squares in FIG. 7), one can see that the pH changes from 6.6 to 4.36 as 1 mL of acid is added in 0.1 mL increments. The pH of this solution hits the pKa after 0.6 mL of 25 mM HCl is added; this is the point of maximum buffering capacity. Although it is difficult to clearly discern by eye, the pH change (4.81 to 4.74) is minimized as an additional 0.1 mL acid is added (i.e., going from 0.6 mL to 0.7 mL as compared to any other addition of 0.1 mL acid). This is the experimental illustration of the maximum buffer capacity that can be calculated from the Van Slyke buffer equation:

$$\beta = 2.3C \frac{K_a[H_3O^+]}{(K_a + [H_3O^+])^2}$$

When calculated the maximum buffer capacity of 10 mM sodium valproate (i.e., at pH=pKa=4.8), one gets a value of 5.75×10-3. For comparison, blood has a buffer capacity of 3.9×10-2. One can see from the graph depicted in FIG. 7 that the change in pH of 150 mg/mL sodium valproate is minimal, indicating that it acts like a buffer well above (>3 pH units) its pKa. FIG. 7 illustrates that the addition of 0.4% sodium citrate has virtually no effect on the buffer capacity of 150 mg/mL sodium valproate. If one looks at the last two points in the titration curve of 150 mg/mL sodium valproate, the pH changes from 7.34 to 7.30, indicating a very strong buffering capacity even though this is 2.5 pH units above the pKa of sodium valproate. According to the Van Slyke equation, the calculated (theoretical) buffer capacity of 150 mg/mL sodium valproate at pH 7.4 is roughly equivalent ($\beta$=5.19×10-3) to that seen in the typical buffer (10 mM) at its maximum buffer capacity (pH=4.8). In short, this demonstrates that 150 mg/mL sodium valproate acts as a buffer at physiological pH (pH=7.4) that is equivalent in strength to the maximum buffer capacity achieved at a "typical" buffer concentration at pH 4.8, and this is consistent with the pH changes upon titration observed. This is unexpected in the sense that this strong buffer capacity is observed well outside of the range expected for a typical buffer solution with a pKa of 4.8. The fact that this is observed is consistent with the equation described above, so it could be argued that this behavior is predicted from basic theory. However, because this high concentration of buffer species is so different from normal buffer solutions it is unexpected, i.e., formulation scientists typically use the "rule of thumb" of ±1 pH unit from the pKa.

Concerns about potential precipitation during administration due to either reduced pH or contaminating metal ions prompted us to explore sodium citrate as both a buffering component and a chelator of metal ions. Because citrate has a pKa of 6.4, incorporation of citrate into sodium valproate solutions should fortify buffering in the physiological pH range. Citrate may chelate trace metal ions that may become solubilized/released within the pump. Considering the unexpectedly strong buffering by sodium valproate (described above), additional buffering capacity may not be necessary. Indeed, results with solutions of 150 mg/mL (0.9 M) sodium valproate with or without 0.4% sodium citrate (13.6 mM) indicate that this low level of citrate does not provide any measurable increase in buffering capacity above pH 7, nor does it significantly change the initial pH of these solutions. Nonetheless, inclusion of sodium citrate as a cation/metal chelator may provide an improved formulation. It is worth noting that citrate is naturally present in cerebral spinal fluid. The natural presence of citrate in cerebral spinal fluid indicates that citrate should be safe when used in a pharmaceutical composition.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Bilateral Infusion Data

PERCEPTION OF BODY TEMPERATURE: Subjects 01-01, 01-03 and 01-04 all have reported they are always cold—every week that is one of the things they mention—initially I think Mark attributed it to the surgery, but I know that No 1 and No 3 are still claiming they always feel cold. It will be interesting to see what they are like when the weather warms up. Number 1 says she has to always put the heater and extra layers on, and sometimes she is so cold her teeth chatter. No 3 is very underweight so but when she comes for refills needs lots of warm blankets and is always wearing lots of layers. No 4 said he was cold for the short time he was receiving the Valproate as well (3 weeks). No 2 hasn't really said she was cold but as discussed, she has some other issues as discussed but I will ask her Friday. I will ask no 5 tomorrow is she feels cold as last week as she has had one week "on" the Valproate and she is currently completing her placebo week so hasn't really had the active treatment for long. The other thing all the patients say when they reach a therapeutic level they also have a feeling of nauseous which seems to pass over time.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The high pH of these solutions suggests that sodium valproate at high concentrations is capable of acting as a buffer well above it pKa. Typically, the useful range of a buffer is estimated to be about 1 pH unit above/below its pKa. Thus, sodium valproate would be expected to be useful as a buffer at pH 3.8-5.8. Accordingly, sodium valproate solutions should have little capacity to resist changes in pH outside of this range. Indeed, it was expected that solutions of sodium valproate could be easily titrated down to physiological pH (7-7.4), and that this would require the addition of a buffer (e.g., phosphate, Tris, citrate) to maintain sodium valproate solutions in the physiological pH range. Unexpectedly, our experiments indicate that these concentrated solutions of sodium valproate strongly buffer solutions at pH>8, and significant quantities of acid are required to lower the pH into the physiological range. Again, considering the pKa of 4.8, one would expect minimal buffering of sodium valproate above pH 6, but this is not the case. Accordingly, concentrated solutions of sodium valproate are not only readily prepared by dissolving at room temperature, they buffer themselves at pH values well above that predicted by their pKa. This unexpected property suggests that highly concentrated aqueous solutions of sodium valproate are homogenous and maintain stable pH; suitable for parenteral administration and prolonged storage within a pump.

Concerns about potential precipitation during administration due to either reduced pH or contaminating metal ions prompted us to explore sodium citrate as both a buffering component and a chelator of metal ions. Because citrate has a pKa of 6.4, incorporation of citrate into sodium alproate solutions should fortify buffering in the physiological pH range. Citrate may chelate trace metal ions that may become solubilized/released within the pump.

Considering the unexpectedly strong buffering by sodium valproate (described above), additional buffering capacity may not be necessary. Indeed, results with solutions of 150 mg/mL (0.9 M) sodium valproate with or without 0.4% sodium citrate (13.6 mM) indicate that this low level of citrate does not provide any measurable increase in buffering capacity above pH 7, nor does it significantly change the initial pH of these solutions. Nonetheless, inclusion of sodium citrate as a cation/metal chelator may provide an improved formulation. It is worth noting that citrate is naturally present in cerebral spinal fluid. The natural presence of citrate in cerebral spinal fluid indicates that citrate should be safe when used in a pharmaceutical composition.

Example 2

Perception of Body Temperature

Subjects 01-01, 01-03 and 01-04 all have reported they are always cold—every week that is one of the things they mention initially I. Mark attributed it to the surgery, but I know that No 1 and No 3 are still claiming they always feel cold. It will be interesting to see what they are like when the weather warms up. Number 1 says she has to always put the heater and extra layers on, and sometimes she is so cold her teeth chatter. No 3 is very underweight so but when she comes for refills needs lots of warm blankets and is always wearing lots of layers. No 4 said he was cold for the short time he was receiving the Valproate as well (3 weeks). No 2 hasn't really said she was cold but as discussed, she has some other issues as discussed but I will ask her Friday. I will ask no 5 tomorrow is she feels cold as last week as she has had one week "on" the Valproate and she is currently completing her placebo week so hasn't really had the active treatment for long. The other thing all the patients say when they reach a therapeutic level they also have a feeling of nauseous which seems to pass over time.

Example 3

Avoid late interaction or degradation related to Titanium Pump

On the development of highly concentrated formulations of sodium valproate:

We initially explored the potential of developing a formulation containing emulsified droplets of pure valproic acid (a liquid) to achieve higher concentrations that the reported solubility limit of sodium valproate (50-100 mg/mL). In the early experiments with the liquid form of valproic acid, it was found that the droplets of valproic acid were dissolving into the water, complicating the development of a stable emulsion (an emulsion is only possible if one phase is not soluble in the other phase). In the course of these experiments, it also became evident that the reported solubility limit of sodium valproate was grossly inaccurate, and we could dissolve very high concentrations in water; up to at least 500 mg/mL. Therefore, it was unnecessary to go through the work of developing a stable emulsion (in fact, this would be quite difficult considering its high solubility), and that high concentrations of the drug could be achieved as a solution. Accordingly, we opted to pursue a single phase solution of highly concentrated sodium valproate.

On the use of citrate in ICV formulations:

Our initial formulations did not include citrate. When problems with the pump were reported, we assumed that the tubing was clogged, and therefore that some precipitation/ aggregation had occurred. Knowing that the formulation was well below the solubility limit of sodium valproate (see above), we then hypothesized about what could be causing a precipitate to form. It is important to recognize that the potential for precipitation/aggregation is increased in very concentrated formulations like those we are developing. Also, it is well-known that metal ions can desorb from any metallic surface, and interact with molecules in solution. Typically, metal ions are desorbed as cationic species that are likely to interact with anionic molecules (e.g., valproic acid). In addition, metal ions can catalyze oxidation reactions (e.g., Fenton chemistry) that degrade the drug molecule into inactive species that may be more prone to precipitation/aggregation. For this reason, excipients that bind metal ions (i.e., chelators) are often used in pharmaceutical formulations to reduce the potential for physical (precipitation) and chemical (oxidation) degradation. In fact, Depacon (an IV-injectable solution of sodium valproate) contains EDTA, and we speculated that this might be added for its ability to chelate metals, thereby stabilizing the solution. In considering a chelator that would be suitable for ICV administration, we were concerned that EDTA would chelate calcium which could interfere with neuronal activity. In searching for other chelators that might be compatible with the brain, we learned that citrate was a natural component of CSF, and thus would be compatible with this route of administration.

In addition to metal-induced precipitation, the other possibility that occurred to us was a precipitation event due to changes in pH. We reasoned that a buffering agent that prevented pH changes would also be beneficial. Since it is advantageous to develop formulations at near physiological pH (well above the pKa of sodium valproate; 4.8), it would be desirable to include a buffer species possessing a higher Kasuch that it would prevent a decrease in pH. In this regard, citrate also served that function, and it has three pKa's (3.13, 4.76 and 6.40) that would allow it to perform a buffering function in addition to its role as a chelator. It was only later that we learned that sodium valproate was capable of buffering itself at much higher pH.

Sodium valproate is used clinically at concentrations of 100 mg/mL. Like any weak acid, the valproate molecule will be charged above its pKa value (4.8), and thus more readily soluble at high pH. Despite its charged character at high pH, solubility limits in water are commonly reported as 50-100 mg/mL. Indeed, this is quite concentrated for any solute, with 100 mg/mL equivalent to a 10% solution. Given the reported solubility limit, we were surprised when our experiments demonstrated that sodium valproate fully dissolves and forms clear, homogeneous aqueous solutions up to at least 500 mg/ml. Furthermore, given a pKa of 4.8, it would be expected that a concentrated solution of sodium valproate would have a pH slightly above the pKa, perhaps even a whole pH unit above this value ($\approx$5.5-6.0). However, a solution of 150 mg/mL sodium valproate in water yields a pH of approximately 8.3. More concentrated solutions (>350 mg/mL) possess pH values above 9. This unexpected finding indicates that sodium valproate is much more soluble than is commonly reported.

In addition, the high pH of these solutions suggests that sodium valproate at high concentrations is capable of acting as a buffer well above its pKa. Typically, the useful range of a buffer is estimated to be about 1 pH unit above/below its pKa. Thus, sodium valproate would be expected to be useful as a buffer at pH 3.8-5.8. Accordingly, sodium valproate solutions should have little capacity to resist changes in pH outside of this range. Indeed, we expected that solutions of sodium valproate could be easily titrated down to physiological pH (7-7.4), and that this would require the addition of a buffer (e.g., phosphate, Tris, citrate) to maintain sodium valproate solutions in the physiological pH range. Surprisingly, our experiments indicate that these concentrated solutions of sodium valproate strongly buffer solutions at pH>8, and significant quantities of acid are required to lower the pH into the physiological range. Again, considering the pKa of 4.8, one would expect minimal buffering of sodium valproate above pH 6, but this is not the case. Accordingly, concentrated solutions of sodium valproate are not only readily prepared by dissolving at room temperature, they buffer themselves at pH values well above that predicted by their pKa. This unexpected property suggests that highly concentrated aqueous solutions of sodium valproate are homogenous and maintain stable pH; suitable for parenteral administration and prolonged storage within a pump.

Concerns about potential precipitation during administration due to either reduced pH or contaminating metal ions prompted us to explore sodium citrate as both a buffering component and a chelator of metal ions. Because citrate has a pKa of 6.4, incorporation of citrate into sodium valproate solutions should fortify buffering in the physiological pH range, and also chelate trace metal ions that may become solubilized/released within the pump. Considering the unexpectedly strong buffering by sodium valproate (described above), additional buffering capacity may not be necessary. Indeed, our results with solutions of 150 mg/mL (0.9 M) sodium valproate with or without 0.4% sodium citrate (13.6 mM) indicate that this low level of citrate does not provide any measurable increase in buffering capacity above pH 7, nor does it significantly change the initial pH of these solutions. Nonetheless, inclusion of sodium citrate as a cation/metal chelator provide an improved formulation. It is worth noting that citrate is naturally present in cerebral spinal fluid.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of ameliorating a symptom of epilepsy in a subject, comprising: administering directly to the brain of a subject a therapeutically effective amount of a medicament multiple times over a time period of at least two days, thereby ameliorating the symptom of epilepsy, determining medicament concentration by sampling cerebrospinal fluid from the lateral ventricle and performing a test of medicament concentration in the sampled cerebrospinal fluid, changing daily flow rate and/or concentration of infused medication to achieve an improvement a clinical symptom, wherein the medicament comprises valproic acid or a pharmaceutically active derivative thereof; wherein the concentration of the medicament is 100-500 mg/mL; wherein the medicament comprises a half-life of less than 2 hours in cerebrospinal fluid and wherein during treatment the medicament has a concentration in the cerebrospinal fluid of between about 1 microgram/ml to 500 micrograms/ml.

2. The method of claim 1, wherein during treatment the medicament has a concentration in the cerebrospinal fluid of between 2 microgram/mL, to 200 microgram/mL; and wherein the administering directly to cerebrospinal fluid of the subject's brain, and is substantially continuous administration of the medicament during treatment via a catheter.

3. The method of claim 2, wherein the administering directly to a subject's brain is via multiple bolus pulses of the medicament during treatment.

4. The method of claim 2, wherein administering directly to a subject's brain is in multiple bolus pulses of the medicament during treatment, and wherein a dosage is based upon a target treatment dosage of the medicament and the medicament's half-life in the cerebrospinal fluid such that the target treatment dosage during a treatment period is multiplied by a number of half-lives lost occurring during gaps in a treatment period to achieve meaningful target therapeutic levels.

5. The method of claim 2, wherein there is a substantially linear relationship between a concentration of the medicament in the cerebrospinal fluid and a daily dosage of the medicament.

6. The method of claim 2, further comprising:
monitoring administration of the medicament by monitoring the subject's perception of their own body temperature.

7. The method of claim 2, wherein the medicament is administered as part of a pharmaceutical composition comprising citric acid.

8. The method of claim 2, wherein the medicament is only administered to one lateral brain ventricle on one side of the brain and not bilaterally administered to both ventricles.

9. A method of ameliorating a symptom of epilepsy comprising: administering a therapeutically effective amount of a medicament with a catheter directly to the brain of a subject, wherein the medicament comprises a half-life of less than 2 hours in cerebrospinal fluid; determining medicament concentration by sampling cerebrospinal fluid from the lateral ventricle and performing a test of the concentration of medicament in the sampled cerebrospinal fluid; and changing daily flow rate and/or concentration of infused medication to achieve an improvement in a clinical symptom, wherein the medicament ameliorates and/or modifies the epilepsy, wherein the medicament comprises valproic acid or a pharmaceutically active derivative thereof, wherein the concentration of the medicament is 100-500 mg/mL and wherein during treatment the medicament has a concentration in the cerebrospinal fluid of between about 1 microgram/ml to 500 micrograms/ml.

10. The method of claim 9, wherein the medicament is in a formulation with a composition, comprising citric acid.

11. The method of claim 10, wherein the medicament concentration is at least 150 mg/mL.

12. The method of claim 10, wherein the medicament concentration is at least 200 mg/mL.

13. The method of claim 10, wherein the medicament concentration is at least 300 mg/mL.

14. A method of ameliorating seizures of a patient diagnosed with epilepsy, comprising: administering directly to cerebrospinal fluid of a patient's brain a formulation comprised of valproic acid or a pharmaceutically acceptable salt thereof; continuing the administration directly to cerebrospinal fluid of the patient's brain over a period of days; determining formulation concentration by sampling cerebrospinal fluid from the lateral ventricle and performing a test of the concentration of the formulation in the sampled cerebrospinal fluid; and changing daily flow rate and/or concentration of infused formulation to achieve an improvement in a clinical symptom, wherein the concentration of the medicament is 100-500 mg/mL; wherein the medicament comprises a half-life of less than 2 hours in cerebrospinal fluid, wherein during treatment the medicament has a concentration in the cerebrospinal fluid of between about 1 microgram/ml to 500 micrograms/ml, and thereby ameliorating seizures.

* * * * *